United States Patent [19]

Juska

[11] Patent Number: 4,572,183

[45] Date of Patent: Feb. 25, 1986

[54] POSITIVE FEED SYSTEM FOR A SURGICAL LIGATING INSTRUMENT

[75] Inventor: Donald D. Juska, Winchester, Ohio

[73] Assignee: Senmed, Inc., Cincinnati, Ohio

[21] Appl. No.: 674,585

[22] Filed: Nov. 26, 1984

[51] Int. Cl.⁴ .................. A61B 17/12; A61B 17/10
[52] U.S. Cl. .................. 128/325; 29/243.56; 227/19; 227/116; 227/DIG. 1 B
[58] Field of Search .................. 128/334 R, 325, 326; 227/DIG. 1, DIG. 1 B, 19, 116; 29/243.56; 72/410

[56] References Cited

U.S. PATENT DOCUMENTS

| | | | |
|---|---|---|---|
| 2,929,069 | 3/1960 | Christin | 29/243.56 X |
| 3,646,801 | 3/1972 | Caroli | 227/19 X |
| 3,665,924 | 5/1972 | Noiles et al. | 227/DIG. 1 X |
| 4,043,504 | 8/1977 | Hueil et al. | 227/DIG. 1 X |
| 4,152,920 | 5/1979 | Green | 128/325 X |
| 4,471,780 | 9/1984 | Menges et al. | 227/19 X |
| 4,480,640 | 11/1984 | Becht | 128/325 |
| 4,500,024 | 2/1985 | Di Giovanni et al. | 227/19 |
| 4,522,207 | 6/1985 | Klieman et al. | 128/325 |
| 4,534,351 | 8/1985 | Rothfuss et al. | 128/325 X |

FOREIGN PATENT DOCUMENTS 2128477  5/1984  United Kingdom .................. 128/326

Primary Examiner—Paul E. Shapiro
Attorney, Agent, or Firm—Frost & Jacobs

[57] ABSTRACT

An improved clip feed system for a surgical ligating instrument of the type having first and second clip-clamping jaws at its forward end, a pair of handles to shift the jaws between open, clip-feeding and closed, clip-clamping positions, an elongated tube-like clip magazine containing a plurality of clips lying in a row, one behind the other, in the same plane and a feeder shoe to constantly urge the row of clips toward the forward end of the instrument and the forwardmost clip to a staging area in front of the magazine, a pusher track parallel to the clip magazine and extending to the forward ends of the jaws, and a pusher actuated by the handles between a retracted clip-receiving position when the handles and jaws are in their clip-clamping positions and an extended position locating a clip at the forward ends of the jaws when the handles and the jaws are in their clip-feeding positions. The improved clip-feed system comprises a plunger normally located in and biased to an unactuated position adjacent the staging area. The plunger is shiftable by the second jaw, as the second jaw moves to its clip-clamping position, to an actuated position wherein the plunger positively shifts the forwardmost clip from the staging area to the pusher track, the plunger returning to its unactuated position when the second jaw is shifted to its open, clip-feeding position.

14 Claims, 16 Drawing Figures

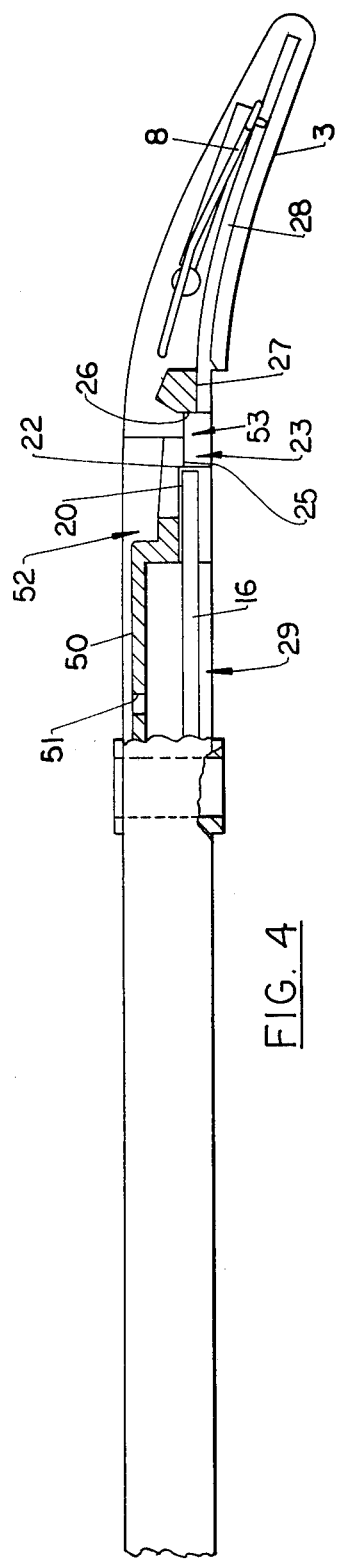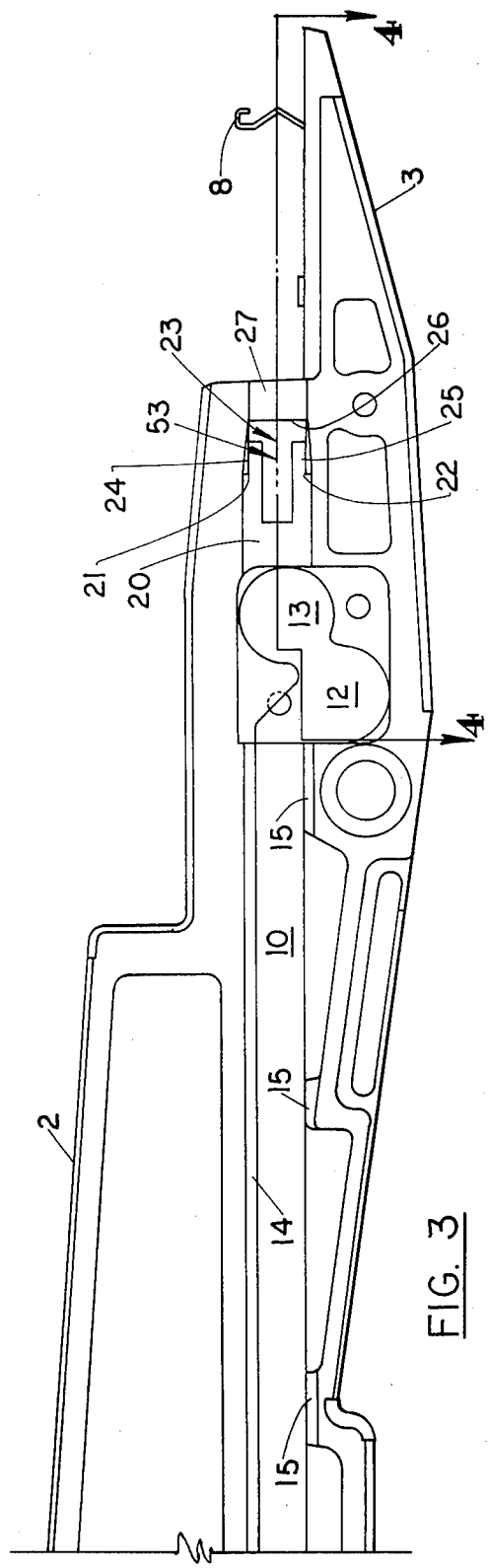

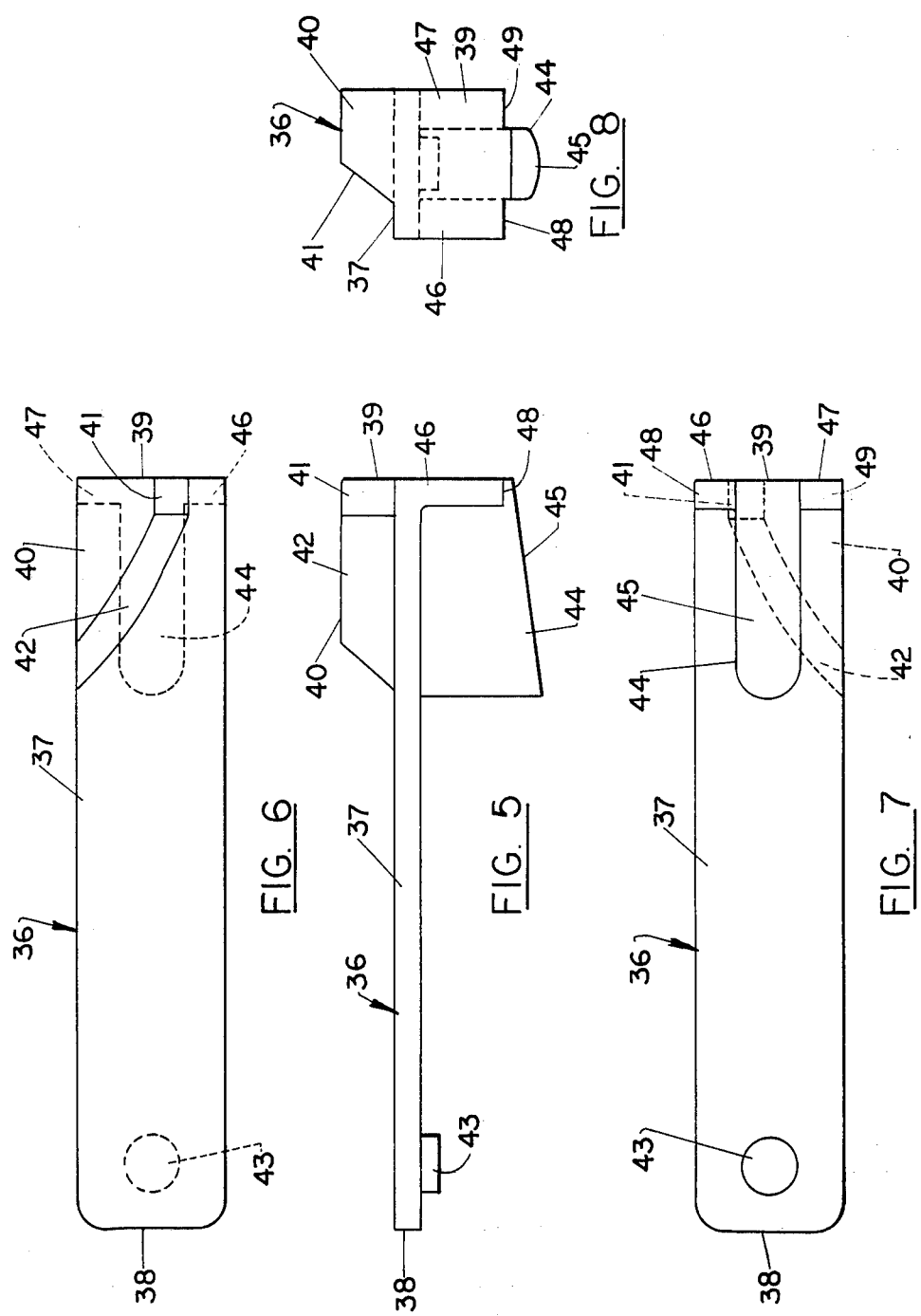

POSITIVE FEED SYSTEM FOR A SURGICAL LIGATING INSTRUMENT

REFERENCE TO RELATED APPLICATIONS

The present invention relates to an improvement in surgical ligating instruments of the general type taught in co-pending application Ser. No. 435,380, filed Oct. 20, 1982, in the names of Robert G. Rothfuss, David K. Kuhl, Federico Bilotti, Hugh Melling and Earl J. Mills, and entitled: LIGATOR, and in co-pending application Ser. No. 546,928, filed Oct. 31, 1983, in the name of James A. Favaron, and entitled: CLIP STOP FOR A SURGICAL LIGATING INSTRUMENT.

TECHNICAL FIELD

The invention relates to an improvement in a surgical ligator for applying clamping clips to veins, arteries, blood vessels and other body tissues, and more particularly to a positive feed system for such a surgical instrument, wherein a plunger shifts the forwardmost clip of a row thereof from a staging area into a pusher track to be shifted by a pusher to the forward ends of the instrument jaws.

BACKGROUND ART

Recently, there has been an increasing number of surgeons using clips, instead of conventional suture ties, to occlude blood vessels and the like. In a typical surgical procedure, many veins, arteries and blood vessels must be tied off, prior to the severing thereof, in order to reach the surgical site. This is an often difficult and time-consuming procedure, since many vessels are located in areas where there is very little room to work. It is important that the occlusion be positive to minimize bleeding, and due to the fact that once severed, the blood-carrying vessels tend to retract into the surrounding tissue and are difficult to retrieve. As used herein and the in the claims, the term "vessel" and "vessels" should be considered in the broad sense to be inclusive of veins, arteries and the like, to which ligator clips are normally applied.

Prior art workers have devised numerous types of surgical ligating instruments designed to clamp blood vessels. There are, for example, reusable, permanent-type ligating instruments, and instruments which are intended to be disposed of after use. There are also ligating instruments wherein each clip is individually loaded in the instrument. Other ligating instruments utilize pre-sterilized cartridges holding a multiplicity of clips. Yet another general class of ligating instruments is provided with a magazine within the instrument, containing a plurality of clips.

The teachings of the present invention are applicable to ligating instruments of the general type having a pair of clamping jaws and a pusher by which a clip is located in position between the jaws, ready to be clamped about a blood vessel or the like. While not intended to be so limited, for purposes of an exemplary showing, the present invention will be described in its application to a disposable surgical ligator of the type taught in the above mentioned co-pending applications Ser. No. 435,380 and Ser. No. 546,928. The teachings of these co-pending applications are incorporated herein by reference.

Briefly, the disposable surgical ligating instrument of co-pending application Ser. No. 435,380 comprises a first handle terminating at its forward end in a first jaw. A second jaw is pivotally mounted to the first handle so as to cooperate with the first jaw. A second handle is pivotally mounted at its forward end to the first handle and is provided with a lug to actuate the second jaw. The handles are shiftable between open and closed positions, and shift the first and second jaws between opened and closed, clip-clamping positions. A magazine in the form of a clip tube, containing a plurality of clips lying one behind the other in the same plane, is mounted in the first handle. A feeder shoe is mounted in the clip tube and constantly urges the row of clips forwardly therein through the agency of a constant-force coil spring. Adjacent and along the clip tube, a pusher is mounted in the first handle in a pusher track which is continued to the forward ends of the jaws. The pusher is shiftable by the first and second handles between a retracted position, when the handles are closed, and an extended position, to locate a clip in the pusher track between the forward ends of the jaws, when the handles are open. The first handle provides a ramp structure leading to the pusher track at the forward end of the clip tube. The ramp structure is covered by the pusher when in its extended position. The ramp is exposed by the pusher when in its retracted position, enabling the forwardmost clip of the row to be transferred from the clip tube, via the ramp, to the pusher track in front of the pusher, due to the forward urging of the clips by the feeder shoe.

When the first and second handles are shifted from their closed to their open positions, the first and second jaws will also shift from their closed to their open positions and the pusher will locate a clip in the pusher track at a position between the forward ends of the jaws, ready for clamping. When the first and second handles are squeezed toward each other to their closed positions, the pusher will shift to its retracted position enabling the next forwardmost clip of the row to be ramped or transferred into the pusher track. Immediately thereafter, the first and second jaws will close, clamping the clip therebetween about the vessel to be occluded. This sequence of events is repeated with each opening and closing of the handles, the clip feeding system requiring no force on the part of the surgeon to accomplish its purpose.

Copending application Ser. No. 546,928 teaches a clip stop in the form of a simple resilient wire member which remains between the jaws at all times. The clip stop prevents each clip from being shoved rearwardly in the pusher track by a vessel during the application of the clip thereto and the clamping of the clip thereabout. In addition, the clip stop assures that the clip is separated from the pusher during the initial part of the clip-applying and clamping operation, when the pusher begins to retract from between the jaws.

It has been found that in the absence of a positive means to shift the forwardmost clip from the tube-like cartridge to the pusher track, misfeeding and/or double feeding can occur. In addition, a non-positive system such as the above noted ramp means requires very precise tolerances. The present invention is based upon the discovery that if a staging area is provided at the forward end of the tube-like magazine and if a jaw-actuated plunger is used to positively shift the forwardmost clip from the staging area to the pusher track, the above noted problems will be eliminated. The positive feed system of the present invention is capable of shifting clips of different shapes. The shape of the plunger may be changed to match the shape of the clip, if required. The positive feed system of the present invention can also be used to feed all sizes of ligator clips, so long as the overall surgical ligating instrument is properly scaled for the size fo clip being used. The feed system is capable of shifting both metallic and non-metallic ligator clips.

DISCLOSURE OF THE INVENTION

According to the invention there is provided an improved positive clip feed system for a surgical ligating instrument. The surgical ligating instrument is of the type having first and second clip-clamping jaws at its forward end, a pair of handles to shift the jaws between an open, clip-feeding position and a closed, clip-clamping position, an elongated tube-like clip magazine containing a plurality of clips lying in a row, one behind the other, in the same plane and a feeder shoe coupled to a constant force spring to urge the row of clips toward the forward end of the instrument and the forwardmost clip to a staging area in front of the magazine, a pusher track parallel to the clip magazine and extending to the forward ends of the jaws, and a pusher actuated by the handles between a retracted clip-receiving position when the handles and jaws are in their closed, clip-clamping positions and an extended position locating a clip at the forward ends of the jaws when the handles and the jaws are in their open, clip-feeding positions.

The improved positive clip-feeding system comprises a resiliently mounted plunger. The plunger is normally located in an unactuated position adjacent the staging area and on the opposite side of the staging area from the pusher track. The resilient mounting of the plunger biases it to this unactuated position.

The plunger is provided with an appropriately shaped lug, contactable by the second jaw such that as the second jaw moves to its clip-clamping position, it will cause the plunger to shift to an actuated position wherein the plunger positively shifts the forwardmost clip from the staging area to the pusher track. At the same time, the plunger restrains the next clip of the row from entering fully into the staging area.

When the second jaw shifts to its open, clip-receiving position, the plunger, by virtue of its resilient mounting, will return to its unactuated position.

BRIEF DESCRIPTION OF THE DRAWINGS

FIG. 3 is a fragmentary bottom view of the first handle first jaw member.

FIG. 4 is a fragmentary side elevational view of the first handle first jaw member, partly in cross section along section line 4—4 of FIG. 3.

FIG. 5 is a side elevational view of the plunger of the present invention.

FIG. 6 is a plan view of the plunger of FIG. 5.

FIG. 7 is a bottom view of the plunger of FIG. 5.

FIG. 8 is an end elevation of the plunger of FIG. 5, as seen from the right of FIG. 5.

DETAILED DESCRIPTION OF THE INVENTION

Figure 1:
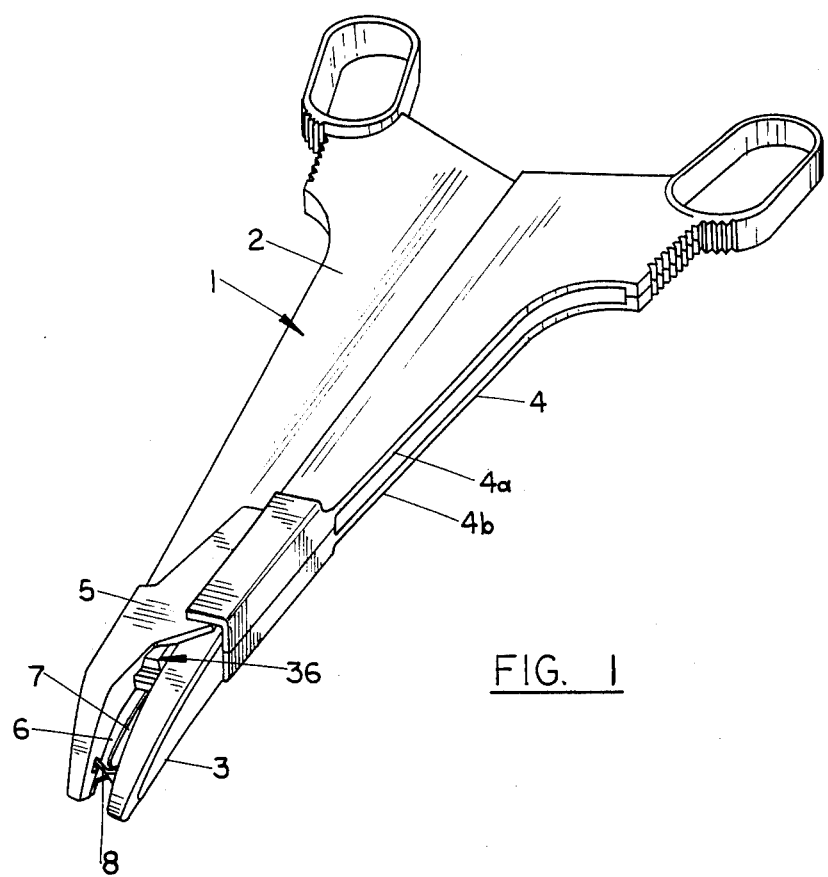
FIG. 1 is a perspective view of an exemplary surgical ligating instrument to which the teachings of the present invention may be applied.

Reference is first made to FIG. 1 wherein an exemplary surgical ligating instrument is shown, of the type set forth in the above noted co-pending applications. The ligating instrument is generally indicated at 1, having a first handle 2 terminating in a first jaw 3 at its forward end. The ligator 1 has a second handle 4 and a second jaw 5. The jaw 5 and the forward end of the second handle 4 are pivotally attached to the first handle 2 in such a way that the second jaw 5 is actuated by the second handle 4. The jaws 3 and 5 each have longitudinally extending slots formed therein (the slot in jaw 5 being shown at 6). These slots constitute a part of the pusher track, as will be apparent hereinafter. In FIG. 1 the pusher is shown at 7 in its forwardmost position. The Figure also illustrates the stop described in the above noted co-pending application Ser. No. 546,928, the clip stop being indicated at 8.

Figure 2:
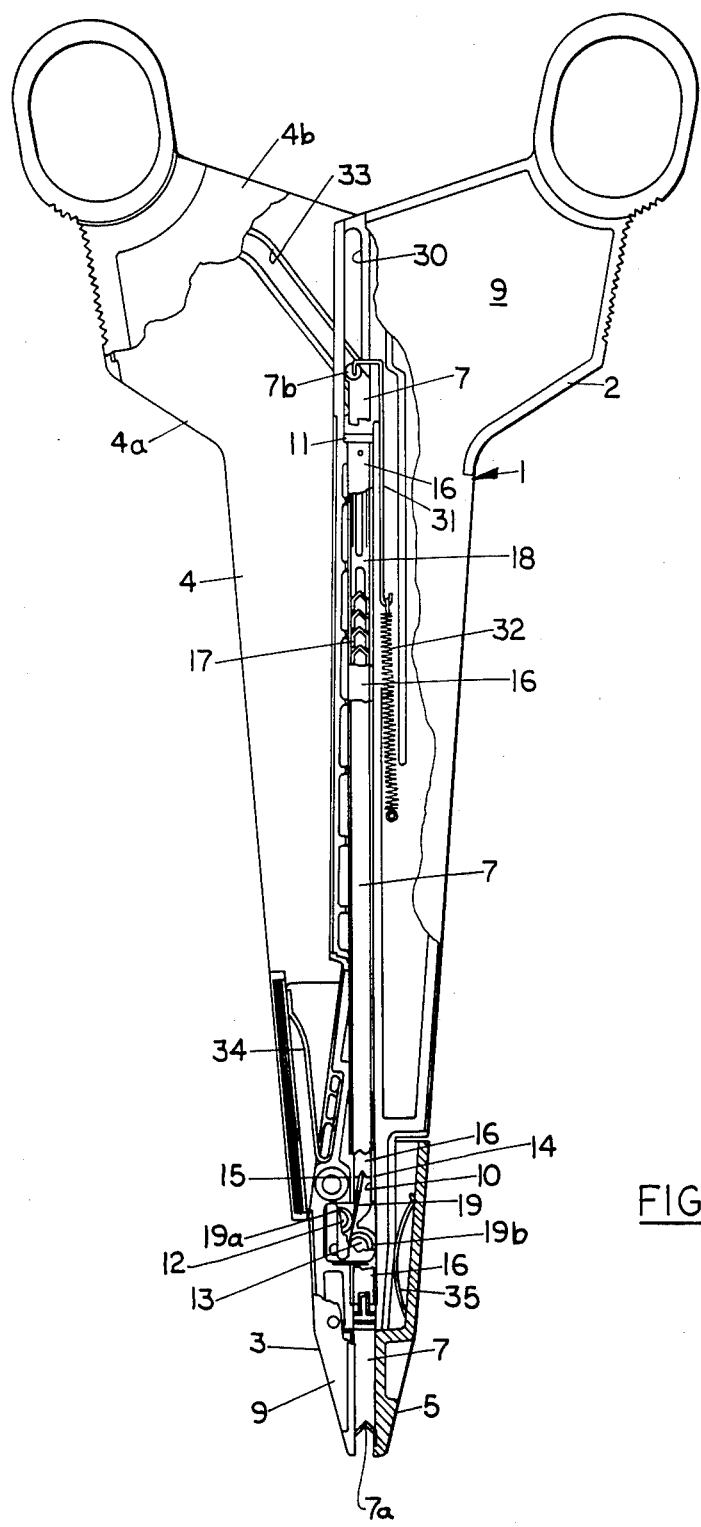
FIG. 2 is a plan view of the instrument of FIG. 1, partly in cross section.

Reference is now made to FIG. 2 wherein the instrument 1 has been rotated 180° about its long axis, with respect to FIG. 1. Like parts have been given like index numerals.

The first handle 2 and the first jaw 3 comprise an integral one-piece plastic member, provided with a metallic cover 9, a portion of which is broken away to show the various elements underneath.

The first handle 2 is provided with a longitudinal channel 10 (see also FIG. 3). The channel 10 terminates at the rearward end of handle 2 in a transverse wall 11. The channel 10 terminates at the forward end of handle 2 in a pair of sockets 12 and 13.

As is described in the above noted co-pending application Ser. No. 435,380, the channel 10 has a ledge 14 extending longitudinaly of one of its edges and a plurality of complimentary ledges 15 extending longitudinally along the other of its edges. Supported on ledges 14 and 15 is a tube-like magazine of C-shaped cross section so as to have a longitudinal slot extending the length thereof. The tube-like magazine is fragmentarily shown in FIG. 2 at 16. Within the tube-like magazine 16 there is a plurality of clips, lying in a plane end-to-end, as shown at 17 in FIG. 2. Behind the row of clips 17 there is a feeder shoe 18 having a lug (not shown) extending downwardly into channel 10 through the longitudinal slot of the tube-like magazine 16. A ribbon-like, constant force spring 19 extends about the lug (not shown) of feeder shoe 18 and has its free ends coiled as at 19a and 19b and located in the sockets 12 and 13 respectively. The spring 19 causes feeder shoe 18 to constantly urge the row 17 of ligator clips toward the forward end of instrument 1 in the tube-like magazine 16.

Referring to FIGS. 3 and 4, the channel 10 continues beyond sockets 12 and 13 at the level of ledges 14 and 15, as shown at 20. This continuation 20 of the upper portion of channel 10 terminates in a pair of transverse abutment surfaces 21 and 22, against which the forwardmost end of tube-like magazine 16 rests, as shown in FIG. 4.

It will be noted that in the area of surface 20 and abutment surfaces 21 and 22, the first handle 2 has a T-shaped opening formed therein and generally indicated at 23. The purpose of the T-shaped opening 23 will be apparent hereinafter. A portion of T-shaped opening 23 bifurcates the surface 20. The bifurcations continue forwardly beyond abutment surface 21 and 22 in surfaces 24 and 25 which, as can be most clearly ascertained from FIG. 4, are coplanar surfaces lying at a level equivalent to an inside surface of the tube-like magazine 16. The forwardmost end of the T-shaped opening 23 is defined by a transverse wall having an abutment surface 26 and an adjacent surface 27 which is coplanar with an outside surface of the tube-like magazine 16. It will be noted that the first jaw 3 has a slot 28 formed therein which is a continuation of the surface 27. The slot 28 in the first jaw 3 is equivalent to the slot 6 in the second jaw 5 (see FIG. 1). The slots 6 and 28, the adjacent surface 27 and the outside surface of the tube-like magazine 16 (within the confines of longitudinal channel 10) form a pusher track, generally indicated at 29, to guide the movement of pusher 7.

Returning to FIG. 2, the forward end 7a of pusher 7 has a V-shaped notch formed therein to generally match the shape of the crown portion of the clips of row 17. The rearward end of pusher 7 terminates in a transverse cylindrical lug 7b. The cylindrical lug 7b rides in a longitudinal opening 30 in first handle 2. The longitudinal opening 30 extends in the same direction as the longitudinal channel 10. A wire-like arm 31 is connected at one end to the cylindrical pusher lug 7b and at the other end to a tension spring 32 anchored in first handle 2. This arrangment biases pusher 7 to its forwardmost clip-feeding position.

Turning to FIG. 1, it will be noted that the second handle 4 is made up of two halves 4a and 4b, the major portions of which, when assembled, are spaced from each other by a distance sufficient to receive a portion of the first handle 2 therebetween. Second handle half 4a is shown in FIG. 2. Second handle half 4b is shown only fragmentarily. The inside surface of handle half 4a has a channel 33 formed thereon. It will be understood that the inside surface of handle half 4b will have a corresponding channel (not shown) formed thereon. The ends of the cylindrical lug 7b of pusher 7 are located in these channels. These channels, together with the elongated opening 30 cooperate with pusher lug 7b such that when the handles 2 and 4 are shifted to their jaw closing positions, the pusher 7 will be shifted rearwardly to its retracted position within first handle 2, with its forwardmost end 7a located just behind the forwardmost end of the tube-like magazine 16. The same elements cooperate to cause the pusher 7 to shift to its forwardmost position (as shown in FIGS. 1 and 2) when the handles 2 and 4 are shifted to their jaw opening positions. When in its forwardmost position, the forward end 7a of pusher 7 is located in jaw slots 6 and 28, or pusher track 29, and is near the forwardmost ends of the instrument jaws 3 and 5.

From the description thus far presented, it will be evident that when the first handle 2 and the second handle 4 are squeezed toward each other the first jaw 3 and the second jaw 5 will close, clamping a ligator clip therebetween about a vessel to be occluded. When the handles 2 and 4 and the jaws 3 and 5 are in their closed clip-clamping positions, the pusher 7 will be in its fully retracted position with its forward end 7a just behind the forward end of the tube-like magazine 16. Upon relaxation of the squeezing force on handles 2 and 4, the handles 2 and 4 and the jaws 3 and 5 will shift to their open, clip-feeding positions under the influence of biasing springs 34 and 35. As the handles 2 and 4 and the jaws 3 and 5 shift to their open, clip-feeding positions, the pusher 7 will shift forwardly, picking up the forwardmost ligator clip of the tube-like magazine 16 and shoving the ligator clip in the pusher track to the forwardmost ends of jaws 3 and 5. The instrument is then ready for the next application of a ligator clip to a vessel to be occluded.

The problem to which the present invention is directed relates to the shifting of the forwardmost ligator clip of the tube-like magazine 16 from the level of the magazine 16 to the level of the adjacent pusher track 29 (see FIG. 4). To accomplish this in a direct and positive manner, a plunger is provided. The plunger is illustrated in FIGS. 5 through 8 and is generally indicated at 36.

The plunger 36 comprises an integral one-piece member, and lends itself well, when the instrument 1 is a disposable surgical ligating instrument, to be molded of plastic material suitable for use in a surgical environment and capable of being sterilized by at least one of the sterilization methods well known in the art. The plunger 36 comprises an elongated, resilient, planar body portion 37 having a rearward end 38 and a forward end 39. On the upper surface of the plunger (as viewed in FIGS. 5 through 8) the body 37 has an upstanding lug 40. To one side, the lug 40 has a first planar sloping surface 41 and a second, adjacent, arcuate sloping surface 42. The purpose of lug 40 and its sloping surfaces 41 and 42 will be apparent hereinafter.

On its lower surface (as viewed in FIGS. 5 through 8), near its rear end 38, the body portion 37 of plunger 36 has a circular lug or boss 43. At the forward end of the lower surface (as viewed in FIGS. 5 through 8) of plunger body 37 there is a centrally located, longitudinally extending wall 44, the forwardmost end of which is coplanar with the forward end 39 of body portion 37. As is most clearly seen in FIG. 5, the bottom edge 45 (as viewed in FIGS. 5 through 8) of wall 44 slopes from the rearward end of wall 44 to the forward end of wall 44. To either side of wall 44 there are transverse wall members 46 and 47, the forward faces of which are coplanar with the forward end of wall 44 and the forward end 39 of body portion 37, as well as the forward end of lug 40. Wall portions 46 and 47 terminate in surfaces 48 and 49, respectively, as shown in FIGS. 5, 7 and 8.

Figure 9:
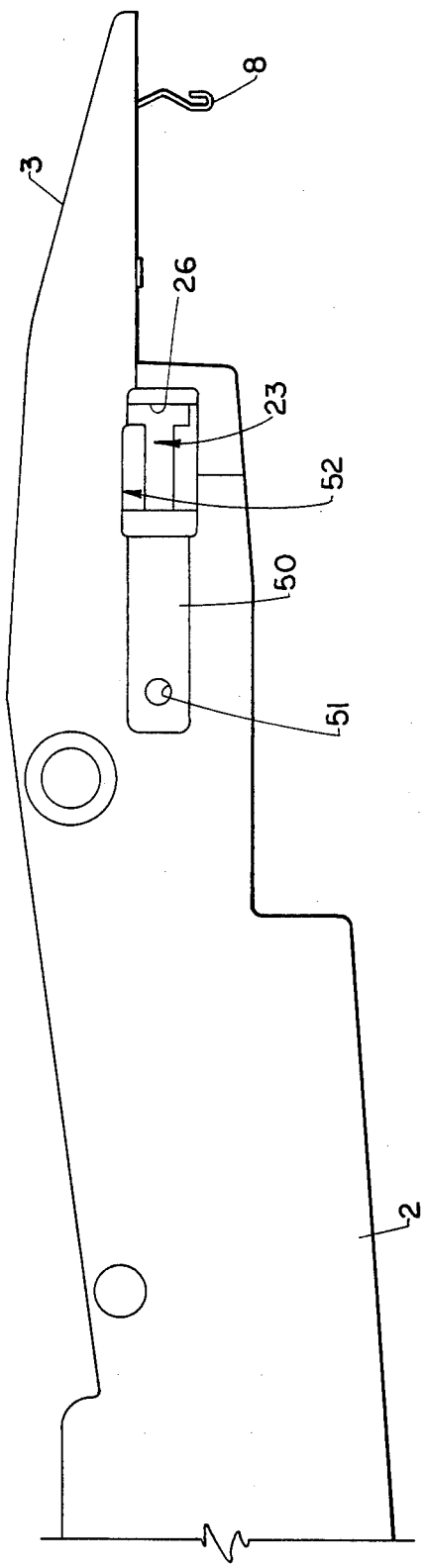
FIG. 9 is a fragmentary plan view of the first handle first jaw member of the present invention.

Reference is now made to FIGS. 5, 6 and 9. FIG. 9 is similar to FIG. 3, but in FIG. 9 the first handle 2 and the first jaw 3 have been rotated 180° with respect to FIG. 3. As is shown in FIG. 9, the outside surface of first handle 2 is provided with an elongated shallow depression 50 (see also FIG. 4). The depression 50, near its rearward end, is provided with a perforation 51. At its forward end, the depression 50 terminates in a somewhat wider, deeper depression, generally indicated at 52. It will be noted that the abutment surface 26 is visible in depression 52, as is the T-shaped perforation 23 and the bifurcations which carry, on their other side, surface 20, abutment surfaces 21 and 22 and surfaces 24 and 25 (see FIG. 3). The depressions 50 and 52 are intended to house plunger 36.

Figure 10:
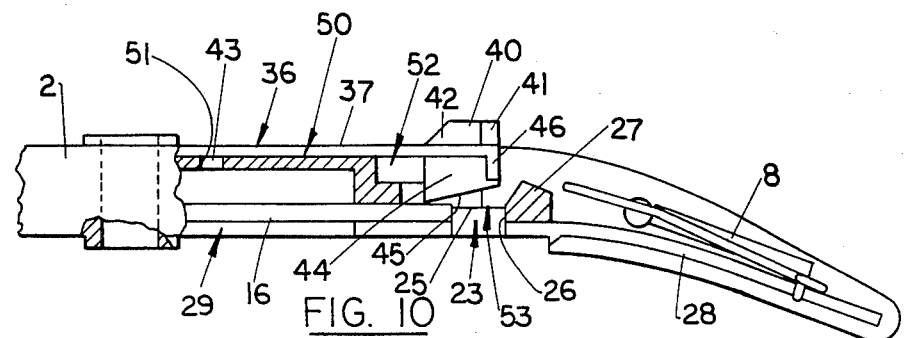
FIG. 10, is a fragmentary side elevational view, partly in cross section, of the first handle-first jaw member, similar to FIG. 4, and showing the plunger in its normal retracted position.

Reference is now made to FIG. 10. FIG. 10 is similar to FIG. 4, with the exception that it shows plunger 36 mounted in depressions 50 and 52. The shallow depression 50 accommodates the majority of the long, thin, resilient body portion 37 of plunger 36 with the circular plunger lug 43 mounted in perforation 51. The longitudinal wall portion 44 and the transverse wall portions 46 and 47 of the forward end of plunger 36 are accommodated in the larger depression 52.

In FIGS. 3, 4 and 10, the area in first handle 2 immediately ahead of the tube-like magazine 16, up to abutment surface 26, above bifurcation surfaces 24 and 25 and below pusher track 29 may be considered a passage means or a staging area and is generally designated in these Figures by index numeral 53. In FIG. 10, the plunger 36 is shown in its normal, unactuated position. It will be noted that when the plunger is in this position, the longitudinal wall portion 44 and the transverse wall portions 46 and 47 do not enter staging area 53. Furthermore, the plunger lug 40, with its planar sloping surface 41 and its arcuate sloping surface 42, is located beyond the outside surface of first handle 2.

Figure 11:
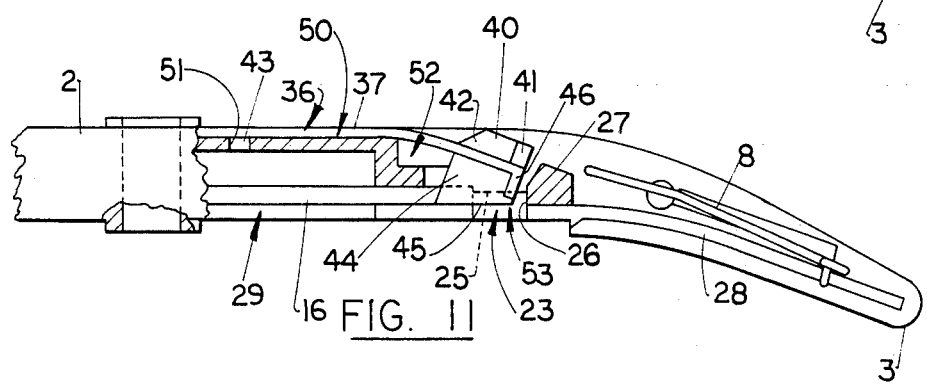
FIG. 11 is a fragmentary side elevational view, partly in cross section, similar to FIG. 10 and illustrating the plunger in its actuated position.

Reference is now made to FIG. 11. FIG. 11 is substantially identical to FIG. 10, but illustrates the plunger 36 in its actuated position. It will be noted that when the plunger is in its actuated position, its longitudinal wall portion 44 and transverse wall portions 46 and 47 have entered the staging area 53 through T-shaped perforation 23. Furthermore, the plunger lug 40 with its planar sloping surface 41 and its arcuate sloping surface 42 has completely entered the larger depression 52 and no longer extends beyond the outer surface of second handle 2. Finally, it will be noted that the sloped surface 45 of the longitudinal wall 44 is substantially coplanar with the pusher track 29. The plunger 36 is enabled to achieve the position shown in FIG. 11 by virtue of the fact that the forward end of the tube-like magazine 16 is notched to accommodate the rearward part of longitudinal plunger wall portion 44.

Figure 12:
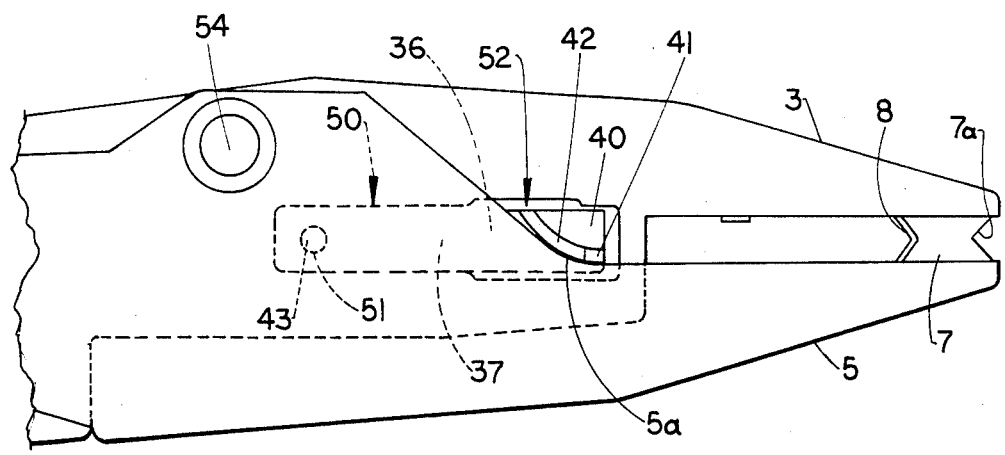
FIG. 12 is a fragmentary plan view of the first handle first jaw member, similar to FIG. 9, and illustrating the second jaw and the plunger mounted thereon.

Reference is now made to FIG. 12. FIG. 12 is similar to FIG. 9, with the exception that the second jaw 5 is shown pivotally mounted as at 54 to the first handle 2. The second jaw 5 and the first jaw 3 are shown in their open, clip-receiving positions with the pusher 7 in its forwardmost position. It will be noted that when second jaw 5 is in its open, clip-receiving position, it covers all of shallow depression 50 and a major portion of larger depression 52, covering all of plunger 36 except its lug 40, with its planar sloping surface 41 and arcuate sloping surface 42. It will be evident from FIG. 12 that as the second jaw 5 shifts toward first jaw 3 and to its closed, clip-clamping position, the edge portion 5a of second jaw 5 will over ride the plunger lug 40, first contacting the planar sloping surface 41 thereof and thereafter contacting the arcuate sloping surface 42 thereof. In this manner, the plunger 36 is shifted from its normal position shown in FIG. 10 to its actuated position shown in FIG. 11. The elongated body portion 37 of plunger 36, being resilient in nature will cause the plunger to return to its normal, unactuated position as shown in FIG. 10 when jaw 5 is returned to its open, clip receiving position.

The overall instrument 1 having been described in sufficient detail, and the elements of the positive feed system having been described in complete detail, the mode of operation of the feed system will now be set forth. When a new instrument is initially handed to the surgeon in the operating room, the instrument handles 2 and 4 and the jaws 3 and 5 will be in their open clip-feeding positions, with the pusher 7 in its forwardmost position, its end 7a being between the forward ends of the jaws 3 and 5. However, since the instrument has not been used before, there will be no ligating clip at the forward end of the jaws.

Figure 13:
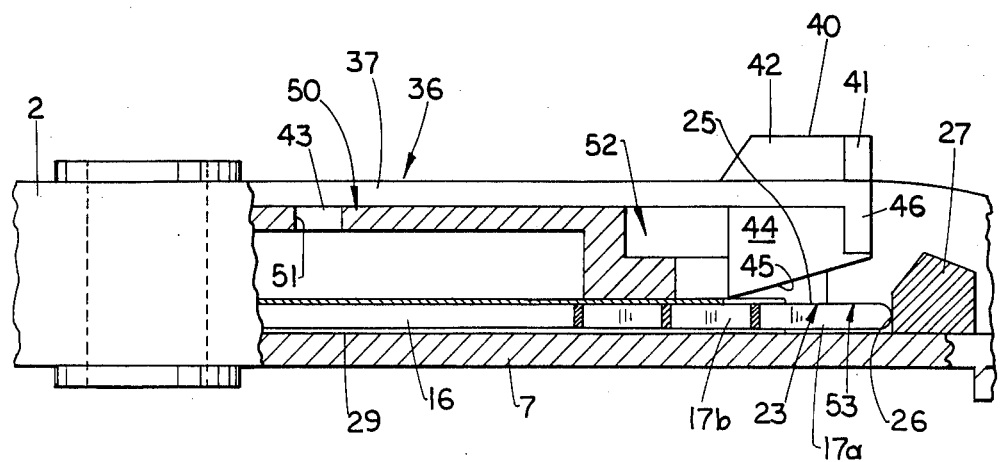
FIG. 13 is an enlarged fragmentary side elevational view of the first handle first jaw member, similar to FIG. 4, with the plunger added and illustrating the initial condition of an instrument at the beginning of a cycle.
Figure 14:
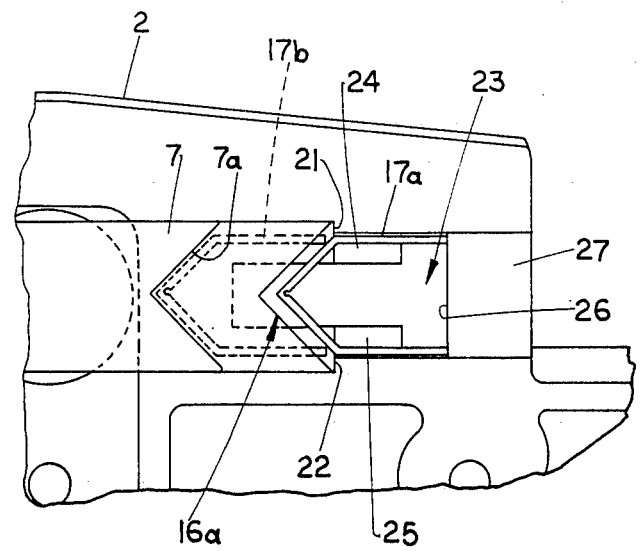
FIG. 14 is an enlarged fragmentary bottom view of the first handle-first jaw member, similar to FIG. 3 and showing the pusher in its retracted position.

It will be remembered from above that the row 17 of ligating clips in the tube-like magazine 16 are constantly urged forwardly in the tube by virtue of feeder shoe 18 and constant force spring 19. Within the tube-like magazine 16, the crown of each ligating clip is engaged by the leg members of the next succeeding ligating clip, except for the last clip in the row 17, which has its crown engaged by the feeder shoe 18. As is most clearly shown in FIGS. 13 and 14, the forwardmost clip 17a of the row 17 is located in the staging area 53 with its legs supported on surfaces 24 and 25. The forwardmost ends of the legs of the forwardmost clip 17a engage the abutment surface 26. The crown portion of the forwardmost clip 17a is just within the confines of the tube-like magazine 16 and is exposed therein by the V-shaped notch 16a in the forwardmost end of magazine 16 (see FIG. 14).

In order for the surgeon to locate the forwardmost ligator clip 17a between the forward ends of jaws 3 and 5, it is only necessary for the surgeon to squeeze or shift the handles 2 and 4 (and thus the jaws 3 and 5) toward each other to their clip-clamping positions. The channels in handle 4, one of which is shown at 33 in FIG. 2, are so configured that the pusher lug 7b will ride in them in such a manner that the pusher 7 will be nearly completely retracted before the jaws 3 and 5 close. As a result of this, the forwardmost end 7a of pusher 7 is located just behind the forwardmost end of the tube-like magazine 16 when the jaw 5 begins to be shifted by handle 4.

Figure 15:
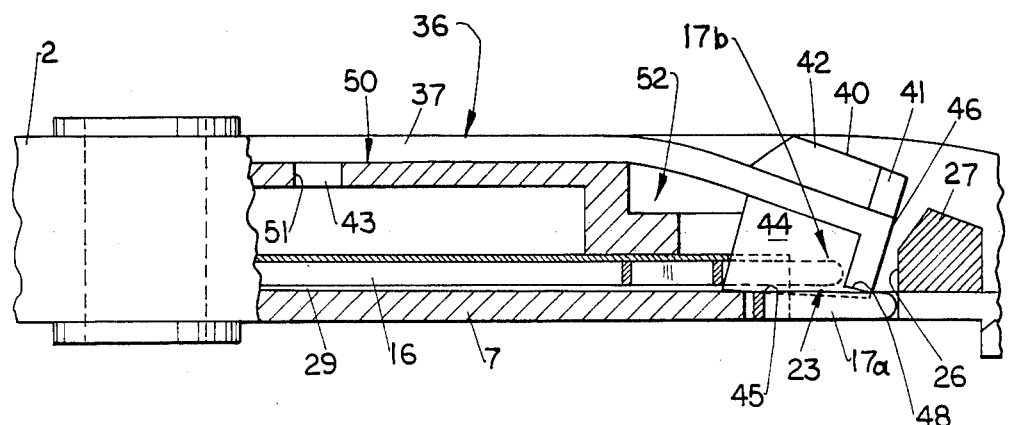
FIGS. 15 and 16 are enlarged fragmentary views, similar to FIG. 13, and illustrating the sequential steps of the positive feed system of the present invention.

When the jaw 5 is shifted by handle 4, the jaw edge 5a will first engage the sloped plunger surface 41, and then the sloped plunger surface 42 causing the plunger 36 to shift through the T-shaped perforation 23 and the staging area 53. This is illustrated in FIG. 15. By virtue of its sloped surface 45, the rearward end of plunger wall 44 will first enter the notch in the tube-like magazine 16, the rearward end of plunger wall 44 ultimately acting as a stop for the clip 17b immediately behind the forwardmost clip 17a. Continued movement of plunger 36 will cause the surface 45 to engage the crown portion of the forwardmost clip 17a and the surfaces 48 and 49 of the transverse wall portions 46 and 47 of plunger 36 to engage the legs of the forwardmost clip 17a. When the plunger is fully shifted to its actuated position, the surfaces 45, 48 and 49 of plunger 36 will be substantially parallel to and coplanar with pusher track 29 and the forwardmost clip will be located in pusher track 29, ready to be engaged and shifted forwardly by pusher 7. It will be apparent from FIG. 15 that the second clip 17b of row 17 has begun to shift into staging area 53 with the forward portions of its legs supported on surfaces 24 and 25. However, this second clip 17b is precluded from completely entering staging area 23 by virtue of the abutment of its crown portion against the rear surface of plunger wall 44. In this manner, the second clip 17b is stopped from being fed along with the first clip 17a into the pusher track 29, and the second clip 17b cannot cause any jamming of the first clip 17a.

Figure 16:
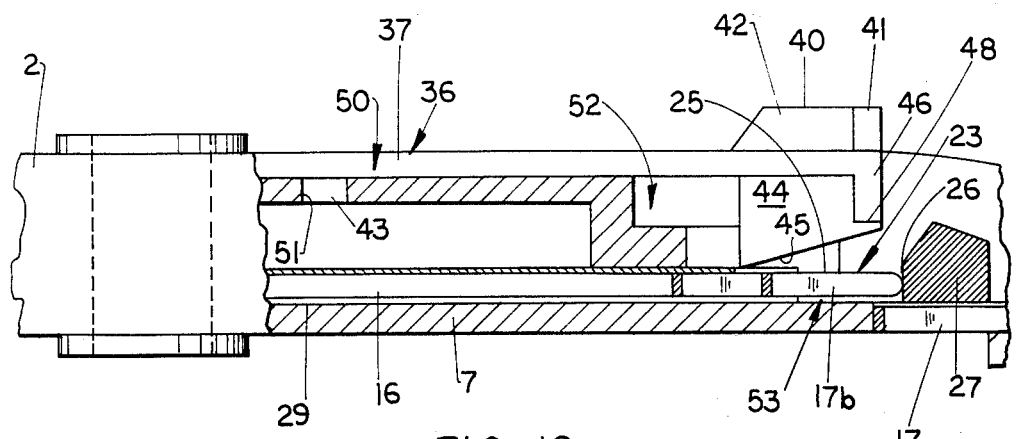

Upon release of the squeezing force on handles 2 and 4, they will be automatically shifted to their open, clip-feeding positions by spring 34 and the jaws 3 and 5 will also achieve their clip-feeding positions, by virtue of handle 2 and spring 35 (see FIG. 2). The pusher 7 will also shift to its forwardmost position automatically, and without any effort on the part of the surgeon. It will be remembered that when the handles 2 and 4 are shifted to their clip-clamping positions, the pusher 7 will retract before the jaws 3 and 5 close. In similar fashion, the jaws 3 and 5 will open before the pusher automatically shifts to its forwardmost position when the squeezing force is released from the handles 2 and 4. The automatic movement of pusher 7 will locate the forwardmost clip 17a at the forward ends of jaws 3 and 5. Furthermore, the shifting of jaw 5 to its open, clip-receiving position will cause the plunger 36 to return to its normal position, as shown in FIG. 16, allowing clip 17b to fully enter staging area 53.

The first squeezing of the handles 2 and 4 of a new instrument to their clip-clamping positions, followed by release of the squeezing force on the handles 2 and 4 will cause the forwardmost clip to be fed to its clip-clamping position as just described. From this point on, the cycle can be repeated for as many times as there are clips in magazine 16. Each time the surgeon squeezes the handles 2 and 4 to their clip-clamping positions, the jaws will clamp a clip about a vessel and at the same time the pusher 17 will retract and the plunger 36 will locate the next clip in the pusher track. Upon release of the squeezing force by the surgeon on handles 2 and 4, the jaws 3 and 5 will return to their open, clip-receiving positions, the plunger will return to its normal retracted position and the pusher will locate the next ligating clip at the forward ends of jaws 3 and 5. It will be apparent that the feeding is positive and the possibility of misfeeds or double feeds is eliminated.

Modifications may be made in the invention without departing from the spirit of it.

What is claimed is:

1. A ligating instrument for applying clamping clips to blood vessels, said instrument comprising a first handle terminating at its forward end in a first jaw, a second handle and a second jaw both coupled to said first handle, said first and second handles being manually shiftable between open and closed positions, said first jaw being shiftable by said first handle and second jaw being shiftable by said second handle between open and closed clip-clamping positions, an elongated magazine, a row of clips located within said magazine, clip feed means mounted within a clip feed track, said clip feed track being parallel to and adjacent to said magazine and extending to the forward ends of said first and second jaws, said clip feed means being shiftable by said first and second handles between a retracted position removed from said jaws when said handles are in their closed positions and an extended clip-locating position between said jaws when said handles are in their open positions, passage means connecting said magazine and said clip feed track, and means for transferring each clip from the forward end of said magazine to said clip feed track via said passage means, said transfer means comprising a plunger normally located in an unactuated position adjacent said magazine, said plunger being shiftable by one of said jaws from said unactuated position to an actuated position within said magazine to shift said forwardmost clip through said passage means into said clip feed track upon closing of said handles whereby said forwardmost clip can be delivered to said forward ends of said first and second jaws by said clip feed means when said handles return to said open position.

2. The instrument claimed in claim 1, further including biasing means to return said plunger to said unactuated position when said jaws return to said open position.

3. The instrument claimed in claim 1, wherein said passage means is blocked by said plunger when said plunger is in said actuated position such that the next succeeding clip is prevented from entering said clip feed track.

4. The instrument claimed in claim 3, wherein said plunger comprises an elongated resilient body, means for attaching said plunger to said instrument, means located at the forward end of said body to engage the forwardmost clip contained in said magazine, and means located on the opposite side of said body from said clip engaging means for contacting said jaw.

5. The instrument claimed in claim 4, wherein said clip engaging means comprises a longitudinal wall with a forward end and a rearward end and a pair of lateral walls adjacent said longitudinal wall forward end, said longitudinal wall being configured to engage the crown portion and said lateral walls being configured to engage the legs of the forwardmost clip in said magazine when said plunger is in said activated position.

6. The instrument claimed in claim 5, wherein said rearward end of said longitudinal wall is configured to contact the crown of the next succeeding clip in said magazine when said plunger is in said activated position to prevent movement of said clip into said passage means.

7. The instrument of claim 6, wherein said jaw contacting means comprises an upstanding lug containing a cam surface which cooperates with said jaw to shift said plunger between said unactuated and said actuated positions.

8. A positive clip feed system for a surgical ligating instrument of the type having first and second jaws at its forward end, first and second handles shiftable between open and closed positions to shift said jaws between open, clip-feeding and closed, clip-clamping positions respectively, a magazine having a forward end and containing a row of clips and means to constantly urge the row of clips toward said forward end of said magazine, a pusher track adjacent said forward end of said magazine and extending to the forward ends of said jaws, and a pusher in said pusher track with a forward end, said pusher being shiftable by said handles between a retracted position with its forward end behind said forward end of said magazine when said handles and said jaws are in their closed positions and an extended position with its forward end adjacent the forward ends of said jaws when said handles and jaws are in their open positions, said positive clip feed system comprising a staging area in said instrument adjacent said forward end of said magazine, said clip urging means locating the forwardmost clip of said row in said staging area, and a plunger normally located in an unactuated position outside said staging area, said plunger being shiftable by one of said jaws from said unactuated position to an actuated position within said staging area to shift said forwardmost clip from said staging area into said pusher track when said last mentioned jaw is shifted to its closed position, and biasing means to return said plunger to its unactuated position when said last mentioned jaw returns to its open position, whereby said forwardmost clip in said pusher track can be engaged and shifted to the forward ends of said jaws by said forward end of said pusher when said pusher is in its extended position.

9. The positive feed system claimed in claim 8, wherein said plunger comprises an elongated resilient body having forward and rearward ends, means at the rearward end of said plunger to attach said plunger to said instrument, an extension on one side of said body near said forward end thereof to engage the forwardmost clip in said staging area, a lug on said body near said forward end thereof and on the opposite side thereof from said extension for contact by said jaw shifting said plunger between said unactuated and actuated positions, said elongated resilient body comprising said plunger biasing means.

10. The positive clip feed system claimed in claim 8, wherein said magazine comprises an elongated member having said forward end, said row of clips lying in said magazine one behind the other in the same plane, said pusher track extending parallel to and adjacent said magazine, said staging area in said instrument being defined on one side by said feeder track with which it communicates and on the other side by a pair of spaced, parallel, clip-supporting surfaces parallel to said feeder track and coplanar with the adjacent inside surface of said magazine, said staging area having a rearward end defined by the forward end of said magazine and a forward end defined by a clip abutment surface perpendicular to said pair of clip supporting surfaces and said pusher track and spaced forwardly of said pair of clip supporting surfaces, said staging area having a depth substantially equivalent to the thickness of a clip, said clip supporting surfaces and said clip abutment surface defining an opening for entrance of said plunger into said staging area.

11. The positive feed system claimed in claim 10 wherein said plunger comprises an elongated resilient body having forward and rearward ends, means at the rearward end of said plunger to attach said plunger to said instrument, an extension on one side of said body near said forward end thereof to engage the forwardmost clip in said staging area, a lug on said body near said forward end thereof and on the opposite side thereof from said extension for contact by said jaw shifting said plunger between said unactuated and actuated positions, said elongated resilient body comprising said plunger biasing means.

12. The positive feed system claimed in claim 11, wherein each of said clips has a pair of legs joined by a crown portion, said plunger extension comprising a longitudinal wall with a forward end and a rearward end and a pair of lateral walls adjacent said longitudinal wall forward end, said longitudinal wall and lateral walls forming a T-shape, said longitudinal wall being configured to engage the crown portion and said lateral walls being configured to engage the legs of the forwardmost clip in said staging area when said plunger is shifted to said actuated position, said opening defined by said clip supporting surfaces and said clip abutment surface being T-shaped, the rearward end of said plunger longitudinal wall being configured to engage the crown of the next succeeding clip in said row to prevent complete entrance of said next succeeding clip into said staging area until said plunger returns to its unactuated position.

13. The positive feed system claimed in claim 11, wherein said first handle has a forward end terminating in said first jaw, said second jaw being pivotally mounted on said first handle so as to cooperate with said first jaw, said second handle having a forward end pivotally mounted on said forward end of said first handle and having lug means to actuate said second jaw, said magazine, said staging area, said pusher track and said pusher being located in said first handle, said plunger being mounted on said first handle and being shiftable between said actuated and said unactuated positions by said second jaw.

14. The positive feed system claimed in claim 13, wherein each of said clips has a pair of legs joined by a crown portion, said plunger extension comprising a longitudinal wall with a forward end and a rearward end and a pair of lateral walls adjacent said longitudinal wall forward end, said longitudinal wall and lateral walls forming a T-shape, said longitudinal wall being configured to engage the crown portion and the lateral walls being configured to engage the legs of the forwardmost clip in said staging area when said plunger is shifted to said actuated position, said opening defined by said clip supporting surfaces and said clip abutment surface being T-shaped, the rearward end of said plunger longitudinal wall being configured to engage the crown of the next succeeding clip in said row to prevent complete entrance of said next succeeding clip into said staging area until said plunger returns to its unactuated position.

* * * * *